(12) United States Patent
Castaneda, Jr.

(10) Patent No.: US 8,915,267 B2
(45) Date of Patent: Dec. 23, 2014

(54) DEVICE AND METHOD FOR FILLING SYRINGES

(76) Inventor: Rogelio Castaneda, Jr., Brownsville, TX (US)

( * ) Notice: Subject to any disclaimer, the term of this patent is extended or adjusted under 35 U.S.C. 154(b) by 534 days.

(21) Appl. No.: 13/150,753

(22) Filed: Jun. 1, 2011

(65) Prior Publication Data

US 2012/0305130 A1     Dec. 6, 2012

(51) Int. Cl.
*B65B 3/04* (2006.01)
*A61M 5/178* (2006.01)
*A61M 5/315* (2006.01)

(52) U.S. Cl.
CPC ................ *B65B 3/04* (2013.01); *A61M 5/1782* (2013.01); *A61M 5/31556* (2013.01)
USPC .................. 141/2; 141/25; 141/382; 141/383

(58) Field of Classification Search
USPC ............. 141/2, 18, 21, 25–27, 382, 383–384
See application file for complete search history.

(56) References Cited

U.S. PATENT DOCUMENTS

| | | | | |
|---|---|---|---|---|
| 5,908,054 | A | * | 6/1999 | Safabash et al. ................ 141/26 |
| 5,911,252 | A | * | 6/1999 | Cassel ............................ 141/234 |
| 7,174,923 | B2 | * | 2/2007 | Schorn et al. ...................... 141/2 |
| 7,671,014 | B2 | * | 3/2010 | Beals et al. ...................... 514/1.1 |
| 7,703,483 | B2 | * | 4/2010 | Hartman et al. ................. 141/27 |
| 7,897,564 | B2 | * | 3/2011 | Beals et al. ...................... 514/7.6 |
| 8,220,504 | B2 | * | 7/2012 | Hartman et al. ................. 141/27 |
| 2004/0206362 | A1 | * | 10/2004 | Furuichi et al. ............... 128/897 |
| 2008/0105328 | A1 | * | 5/2008 | Desmond .......................... 141/2 |

\* cited by examiner

*Primary Examiner* — Nicolas A Arnett
(74) *Attorney, Agent, or Firm* — Young & Thompson

(57) ABSTRACT

A device and a method for filling syringes, which allows the filling of a syringe with exact dosage of different drugs, by using electronic guns or any other suitable device, without the necessity of using a needle and which may be disconnected from said electronic gun to connect a standard needle for the application of the fluid to a patient.

4 Claims, 2 Drawing Sheets

DEVICE AND METHOD FOR FILLING SYRINGES

BACKGROUND OF THE INVENTION

A. Field of the Invention

This invention is related to devices and methods for filling syringes and, more particularly, to a device and a method for filling syringes which allows to fill a syringe with exact dosages of diverse drugs by means of electronic guns or any other suitable device without the necessity of using a needle.

B. Description of the Related Art

When it is necessary to apply a mixture of drugs to a patient by means of a syringe, it is necessary to introduce the needle of the syringe into the containers of the drugs to be applied. If the needle is not substituted by a new one after filing the syringe with the first drug, the needle already impregnated therewith has to be introduced into the container of the second drug and so on, contaminating said drugs with the drugs of the former container.

On the other hand, if the taken out of drugs need to be very low or exact, (for example 0.05 ml.), the taken out by means of a syringe is very difficult or impossible.

In view of the above, applicant developed a device for filling syringes, comprising, a flexible conduit having a first end having means for connecting the flexible conduit to an adaptor of the syringe and a second end having a rubber coupling cone for connecting the conduit to a needle or to the needle of an electronic gun for filling syringes with exact dosage, and which is disconnected from said electronic gun to connect a standard needle for injecting the medicine to a patient.

The method in accordance with the present invention comprises: connecting an end of a flexible tube to a gun for filling syringes and an opposed end, to the adaptor of the syringe which will be filled; filling the syringe with an exact dosage of drug; disconnecting the flexible tube from the gun for filling syringes, once the syringe has been filled with the exact dosage; and connecting in said opposed end, a standard needle for the application of the drug.

By means of the device and method of the present invention, it is possible to fill a syringe with multiple drugs without contaminating the drug containers, since the filling of the syringe is carried out by means of a gun for filling syringes.

Also, it is possible applying a drug cocktail requiring multiple punctures since it is possible to substitute the needle many times as necessary.

Additionally, by means of the device of the present invention, it is possible to apply micro-foam with needle of different calibers, since for the application of micro-foam it is necessary that the syringe be oriented in a vertical position with the fluid outlet pointing upwards in order to allow the micro-foam to migrate to the portion of the barrel near the fluid outlet so it can be injected to the patient. This type of procedure is impossible to be carried out with a conventional syringe and a needle connected thereto, since when trying to inject the foam with the syringe oriented in a vertical position with the fluid outlet pointing downward, the micro-foam migrates upstream and it will be injecting liquid instead of foam.

SUMMARY OF THE INVENTION

It is therefore a main object of the present invention, to provide a device and a method for filling syringes, which allows filling syringes with exact dosage of different drugs by means of an electronic gun or any other suitable device.

It is another main object of the present invention, to provide a device and a method for filling syringes, of the above described nature, by means of which it is possible to fill syringes with multiple drugs, without contaminating the drug containers, since the filling of the syringe is carried out by means of a gun for filling syringes.

It is an additional main object of the present invention, to provide a device and a method for filling syringes, of the above described nature, by means of which it is possible to apply a cocktail of drugs which require multiple puncturing, since it is possible to substitute the needle many times as necessary.

It is also an additional object of the present invention, to provide a device and a method for filling syringes, of the above described nature, by means of which it is possible to apply foam, with needles having different calibers.

These and other objects and advantages of the present invention will be apparent to those persons having usual skill in the field, from the following detailed description of the invention.

DETAILED DESCRIPTION OF THE INVENTION

Figure 1:
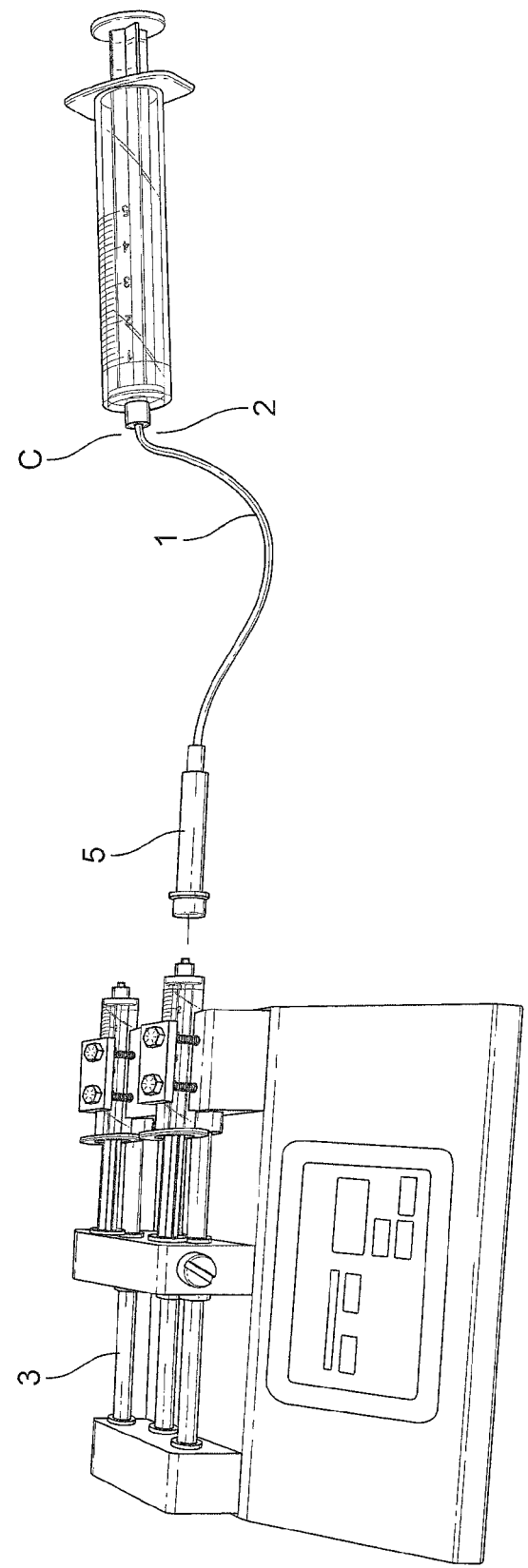
FIG. 1, is a perspective view of the device for filling syringes, of the present invention, connected to an electronic gun for filling syringes.
Figure 2:
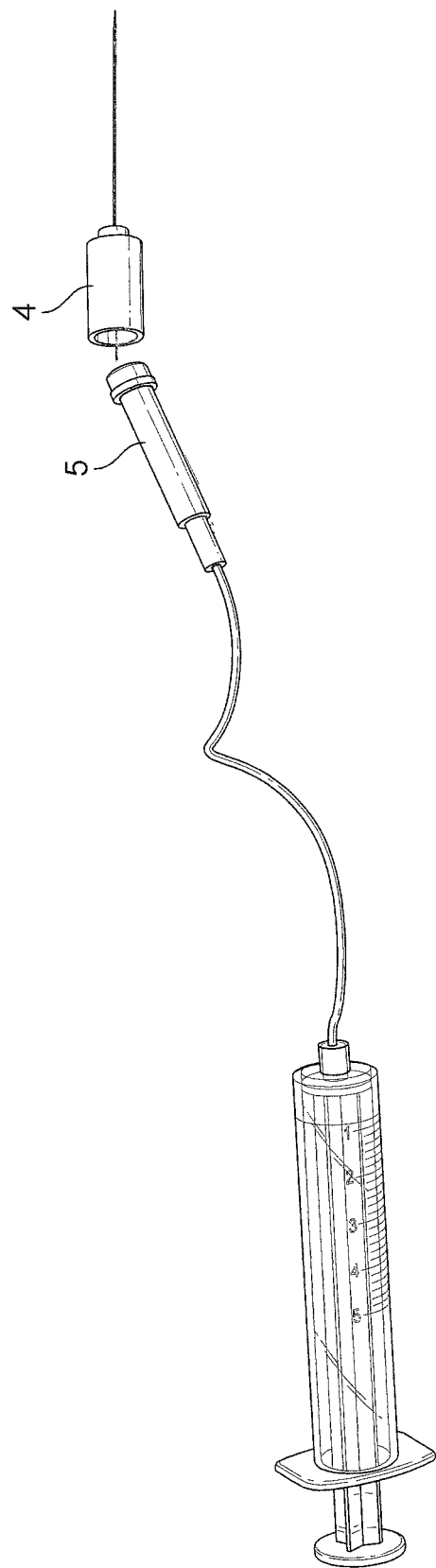
FIG. 2, is a perspective view of the device for filling syringes, of the present invention, having a needle connected for the application of a drug.

The invention will now be described making reference to a preferred embodiment of the invention and to the accompanying drawings. The syringe wherein the device of the present invention can be used, typically comprising a barrel having a first end opened, an adaptor C for receiving the adaptor of a needle at a second end, and a plunger located inside the barrel, to push a liquid, wherein the device for filling syringes, of the present invention, comprising:

a conduit 1 made of a flexible material, preferably of plastic, which has a first and a second end. In a preferred embodiment, the conduit is made of flexible PVC plastic having a length of 100 mm, a width of 1.0 mm and an inner volume of 20 ml.;

means for connecting the conduit to the adaptor C of the syringe, joined to the first end of the conduit 1, comprising a tube of natural or synthetic rubber 2 which is hermetically coupled with said adaptor C. In a preferred embodiment said means for connecting the conduit with the adaptor C are made of poly-isoprene and are joined to the first end of the conduit by means of a cyclohexanone solvent; and means for connecting the conduit to the needle of a gun 3 for filling syringes (FIG. 1) or with a dental needle 4 (FIG. 2), comprising a rubber coupling cone 5, which can be perforated only with needles and which in a preferred embodiment is hermetically connected with the conduit, by means of a cyclohexanone solvent. Said rubber coupling cones 5 are very well known in the art.

In order to fill the syringe with an exact dosage of one or several drugs, one has to follow the following steps:

a) connecting the device to the adaptor C of the syringe;

b) connecting the device to the filling gun 3 by inserting its needle in the coupling cone 5;

c) activating the filling gun 3 for filling the syringe with an exact dosage of drugs;

d) disconnecting the device from the filling gun 3;

e) repeating the steps c) and d) to fill the syringe with exact dosage of other drugs;
f) once that the syringe is filled with the desired drug or drugs, inserting the connection needle of a dental needle 4 to the coupling cone 5 of the device;
g) applying the desired drug or drugs to the patient by means of the dental needle.

Some treatments require multiple punctures with different types of needles, so, thanks to the device of the present invention it is possible to place different types of needle, to apply the dug or drugs.

For creating and applying micro-foam, it should firstly fill the device with the necessary drug or drugs in accordance with steps b) to f) and later the plunger has to be pulled to create a vacuum space. When the plunger is released, the drug is stirred creating little concentration of foams. Once that the micro-foam has been created one can proceed to connect the dental needle for its application to little varicose veins. The syringe has to be oriented in a vertical position, with the fluid outlet pointing upward, to allow the foam to migrate to the fluid outlet so that the foam can be injected to the patient.

It should be understand that the device and method for filling syringes, of the present invention is not limited to the embodiment formerly described and that the persons skilled in the field shall be able, because of the teaching which are here established, to make changes in the device and method for filling syringes of the present invention, which scope shall be exclusively established by the following claims.

What is claimed is:

1. A method for filling syringes, comprising:
   a) providing a flexible conduit having a first end having first means for connecting the flexible conduit to an adaptor of the syringe and a second end having a rubber coupling cone for connecting the conduit to a needle or to the needle of means for filling of syringes;
   b) connecting the device to the adaptor of the syringe;
   c) connecting the device to the filling gun by inserting its needle in the coupling cone;
   d) activating the filling gun for filling the syringe with an exact dosage of drugs;
   e) disconnecting the filling gun from the coupling cone;
   f) once that the syringe is filled with the desired drug or drugs, inserting the connection needle of a dental needle to the coupling cone;
   g) applying the desired drug or drugs to the patient by means of the dental needle.

2. A method for filling syringes in accordance with claim 1, including the additional step of disconnecting the used needle, from the standard syringe coupling cone of the flexible conduit and connecting a new needle to finish the application of the fluid to a patient and repeating said additional step many times as necessary up to applying all the fluid to the patient.

3. A device for filling syringes in combination with a syringe, wherein,
   the syringe comprising i) a cylinder having a first open end and an opposite, second closed end with an adaptor (C), and ii) a plunger inserted in the first open end, and
   said device comprises:
   a syringe filling gun with plural fluid outlets for selectively discharging a drug from each of the fluid outlets;
   a conduit (1) made of a flexible material and with first and second ends;
   a first rubber part, joined to the first end of the conduit, and that hermetically couples the conduit to the adaptor (C) of the syringe; and
   a rubber syringe coupling cone (5) joined to the second end of the conduit, the syringe coupling cone (5) connectable to the fluid outlets of the filling gun, one outlet at a time, for filling the syringe, one drug at a time, and further connectable to a needle (4) for expelling the drugs filling the syringe, from the syringe into a patient,
   wherein, to fill the syringe with plural drugs, a user i) connects the first rubber part to the adaptor (C) of the syringe, ii) connects the coupling cone to a first one of the fluid outlets, iii) activates the filling gun to fill the syringe with a dosage of a first drug, iv) disconnects the coupling cone from the first fluid outlet, v) connects the coupling cone to a second one of the fluid outlets, vi) activates the filling gun to fill the syringe with a dosage of a second drug, and vii) disconnects the coupling cone from the second fluid outlet, and
   wherein, to ready the drug-filled syringe for administration to the patient, the coupling cone (5) is inserted into a connection part of a needle (4).

4. The device of claim 3, wherein the needle (4) is a dental needle.

* * * * *